US006485438B1

(12) United States Patent
Minue

(10) Patent No.: US 6,485,438 B1
(45) Date of Patent: Nov. 26, 2002

(54) CUP TO ASSIST WITH URINE SPECIMEN SAMPLING

(76) Inventor: Jennifer L. Minue, W245 N5722 Partridge La., Sussex, WI (US) 53089

( * ) Notice: Subject to any disclaimer, the term of this patent is extended or adjusted under 35 U.S.C. 154(b) by 17 days.

(21) Appl. No.: 09/675,032

(22) Filed: Sep. 28, 2000

(51) Int. Cl.[7] ............................. A61B 5/00; B65D 81/00
(52) U.S. Cl. ....................... 600/573; 600/574; 604/317
(58) Field of Search ................................. 600/573, 574; 604/317, 318, 322, 329, 349; 215/396, 398; 220/761–766, 771; 73/426; 422/61, 68.1, 82.12, 99

(56) References Cited

U.S. PATENT DOCUMENTS

| | | | | |
|---|---|---|---|---|
| 3,456,283 A | | 7/1969 | Glenn ........................... 16/429 |
| 3,683,452 A | * | 8/1972 | Rickmeier, Jr. et al. ...... 16/445 |
| 3,812,997 A | * | 5/1974 | McNally ...................... 220/529 |
| 4,788,862 A | | 12/1988 | Fuller ........................... 73/426 |
| 5,174,965 A | * | 12/1992 | Jones et al. .................. 422/102 |
| 5,342,330 A | * | 8/1994 | Kane et al. .................. 604/329 |
| D359,883 S | * | 7/1995 | Suarez ......................... D7/533 |
| 5,445,022 A | | 8/1995 | Vassallo ....................... 73/426 |
| 5,558,840 A | * | 9/1996 | Jones et al. .................. 422/104 |
| 6,212,698 B1 | * | 4/2001 | Stingley ........................ 4/315 |

* cited by examiner

Primary Examiner—Kevin Shaver
Assistant Examiner—Charles Marmor, II
(74) Attorney, Agent, or Firm—Joseph S. Heino

(57) ABSTRACT

A disposable urine specimen collection cup has a two-position locking handle incorporated and molded into it. The elongated handle is formed integrally as part of the cup. In its first position, the handle is situated in a generally parallel position relative to the outer surface of the cup. The handle may be located within a recess which is defined along one side of the specimen collection cup. When ready for use, the handle is pulled outwardly from the cup, raised and locked into place. The handle is situated in a generally perpendicular position relative to the outer surface of the cup. The handle folds downwardly against the side of the cup for restorage of the cup and contents after collection of the specimen is completed.

17 Claims, 1 Drawing Sheet

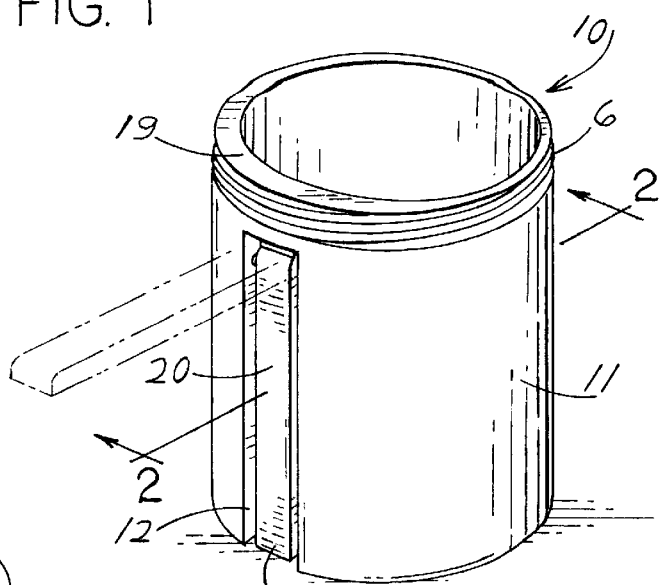
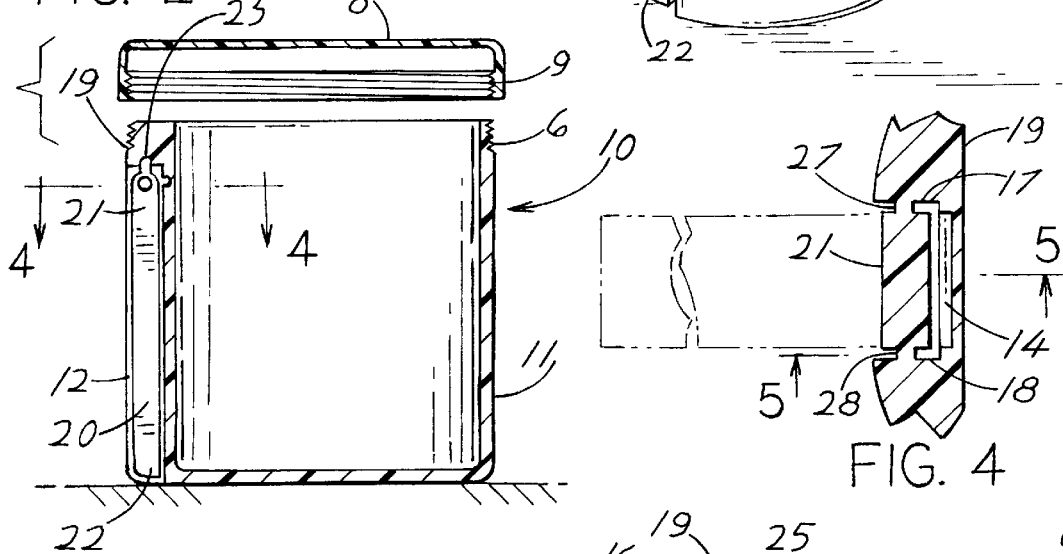
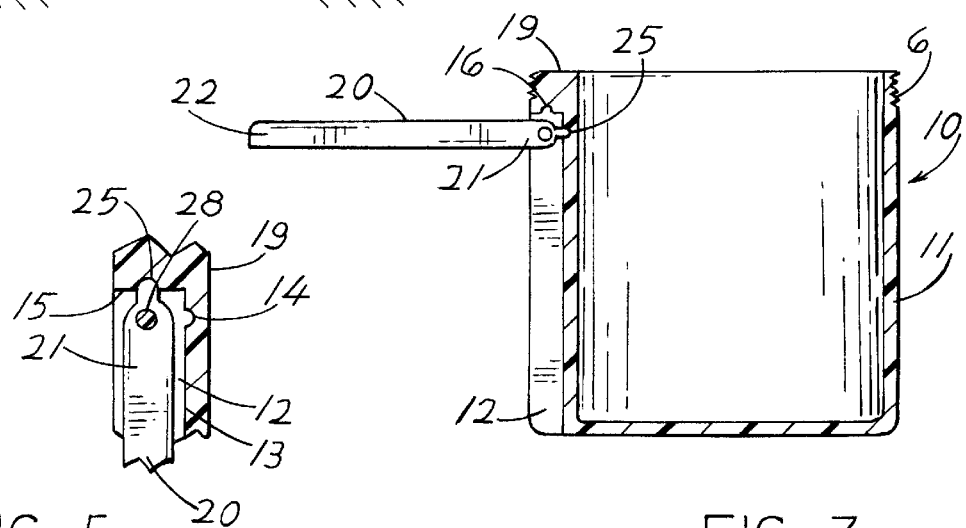

CUP TO ASSIST WITH URINE SPECIMEN SAMPLING

FIELD OF THE INVENTION

This invention relates generally to devices used in the health care industry. More particularly, it relates to a urine specimen collection cup having a retractable support arm for holding the cup in a sanitary, sample-taking orientation relative to the patient when urine specimens are taken.

BACKGROUND OF THE INVENTION

The physical, chemical or microscopic analysis of human urine, or urinalysis, is an essential tool in the health care industry. Urinalysis can provide a wide range of information concerning the health and well being of a patient. The examination of urine color and clarity, the measurement of urine acidity and the detection of the presence of protein, sugar, bacteria and other matters found in urine can tell a great deal about the physical condition of the subject patient.

Urinalysis is performed ideally by using a fresh urine specimen, preferably the first voiding of the day since such specimens are most concentrated and more likely to reveal abnormalities in the urine. All urine tests are also performed ideally by using clean and uncontaminated collection vessels or containers. Additionally, it is recognized that microscopic urinalysis is best performed within the first one-half hour after collection of the specimen since allowing the sample to stand may cause bacterial overgrowth and even dissolution of cellular elements. In short, collection protocol requires that all specimens be collected in sterile containers, sealed against outside contamination and then refrigerated as soon as possible after collection.

Bacteriologic study of urine specimens poses a particular problem due to the inevitable contamination caused by the presence of organisms which reside in the vicinity of the human urethral opening. This contamination can be avoided by catheterization of the urinary bladder, but such is an extreme measure and clearly not recommended for routine examinations. Very reliable bacteriologic urine studies are possible, however, without catheterization by utilizing the so-called "clean-catch mid-stream" technique. For women, collecting a urine specimen in this manner involves partial voiding and then placement of a urinary collection cup between the legs to catch the "mid-stream" urine during continued voiding. This technique is difficult to accomplish without the patient soiling her hands during the urine collection process and without the risk of the patient's hands contacting the collection cup during collection, thus risking inaccurate results due to bacteriologic contamination. In short, eliminating contact with the urine stream simple provides greater hygiene for the patient and reliability for the health care provider charged with handling and measuring the specimen contained within the cup.

SUMMARY OF THE INVENTION

It is, therefore, a principal object of this invention to provide a new, useful and uncomplicated urine specimen collection cup which eliminates the inconveniences, unsanitary practices and ineffective results common with convention urine collection devices. It is another object of this invention to provide such a cup which is manufactured to be disposable. It is still another object of this invention to provide such a cup which allows the patient to more easily hold the cup in specimen-collecting relation to her body and to avoid the risk of dropping the cup into the toilet. It is still another object of the present invention to provide such a cup which would make urine collection easier and more convenient and make patients feel more at ease with the process, thus reducing the stress associated with medical examinations. It is still another object of the present invention to provide such a cup which is particularly beneficial for pregnant or obese women who experience difficulty with reaching around the abdomen to hold a specimen cup. It is still another object of the present invention to provide such a cup which minimizes the risk of contamination thereby avoiding the need to repeat the talking of urine samples and reducing costs to patients and the health care industry in general.

The present invention has obtained these objects. It provides for a disposable urine specimen collection cup which has a two-position locking handle incorporated and molded into it. In the preferred embodiment, the elongated handle is formed within a recess at one side of the specimen collection cup. When ready for use, the handle is pulled outwardly from the cup, raised and locked in place. The handle folds down against the side of the cup for re-storage of the cup and contents after collection of the specimen is completed. The foregoing and other features of the urine sample collection cup of the present invention will be further apparent from the detailed description which follows.

BRIEF DESCRIPTION OF THE DRAWINGS

FIG. 1 shows a front and right side perspective view of a urine sample collection cup constructed in accordance with the present invention and showing a handle member formed within one side of the cup and further showing the handle in its retracted position.

FIG. 2 is a right side elevational and cross-sectioned view of the collection cup shown in FIG. 1 taken along line 2—2 thereof.

FIG. 3 is a right side elevational and cross-sectioned view of the collection cup shown in FIG. 1 and showing the cup handle in its upright and extended position.

FIG. 4 is a enlarged top plan and cross-sectioned view of the cup sidewall and handle in its retracted position as shown in FIGS. 1 and 2.

FIG. 5 is an enlarged right side elevational view of the upper portion of the cup sidewall and handle taken along line 5—5 of FIG. 4.

DETAILED DESCRIPTION

Referring now to the drawings in detail, FIG. 1 shows a urine specimen collection cup, generally identified 10, constructed in accordance with the present invention. As shown in the preferred embodiment, the collection cup 10 includes a cup sidewall 11 which, for a major portion of the circumference of the cup 10 is of a uniform thickness. In the preferred embodiment, one side or portion of the collection cup 10 is formed with a substantially thicker sidewall 19 than the other portions of the cup 10. The purpose of this thicker sidewall 19 to one side of the collection cup 10 is to provide enough material to accommodate a cup recess 12 which is defined within that thicker portion of the cup sidewall 19. The uppermost portion of the collection cup 10 includes external threads 6 which allow for the securement of a cup cover 8 to the cup 10 by means of internal threads 9 defined within the underside of the cover 8. See FIG. 2. In the preferred embodiment, the specimen collection cup 10 is formed from a polystyrene, polypropylene or polyethylene plastic material which may be injection molded. The collection cup 10 may be produced in almost any size with optimum size ranging from eighty (80) to one hundred twenty (120) ml. capacity. Cup sizes may be varied to accommodate these capacity variations.

As shown in FIG. 1, the collection cup 10 also includes a cup handle 20 having a proximal end 21 and a distal end 22. In the preferred embodiment, the cup handle 20 is actually formed integrally as part of the cup 10. When molded, the cup handle 20 is formed in a "handle retracted" position. That is, the handle 20 is formed such that it lies in a plane which is substantially parallel to a tangential plane of the cup side wall 19. See FIG. 2. The cup handle 20 may be urged upwardly from this position and away from the collection cup 10 by placement of a finger within the bottommost portion of the wall recess 12 and by gently lifting the distal end 22 of the handle 20. In this fashion, the cup handle 20 is raised to an upright position which is generally perpendicular relative to a vertical axis of the cylindrical collection cup 10. The proximal end 21 of the cup handle 20 is attached to cup sidewall 19 and within the cup recess 12 by means of a pair of handle attachment members 27, 28. The attachment members 27, 28 extend from the side surfaces 17, 18, respectively, of the sidewall recess 12. As the cup handle 20 is urged upwardly, the attachment members 27, 28 actually deform in a "twisting" or torque-like fashion. This twisting is not sufficient to fracture or break the attachment members 27, 28 away from the side surfaces 17, 18 but is sufficient to provide some resistance when the cup handle 20 is urged upwardly. The resilient nature of the plastic material from which the cup 10 and handle 20 are formed allows for this deformation. Although the handle 20 of the present invention is formed within the cup recess 12 in the preferred embodiment, it is to be understood that the handle 20 could also be formed along the outer surface of the cup side wall 19, tie handle attachment members 27, 28 extending outwardly from the cup sidewall 19 as well. It is also to be understood that the handle 20 could include ridges or other features which could facilitate grasping of the handle 20 (not shown), such is not a limitation of the invention herein.

As formed, the proximal end 21 of the cup handle 20 of the preferred embodiment also includes a locking ridge 25. This locking ridge 25, in turn, rests within an indent 16 which is formed within the top surface 15 of the wall recess 12 when the cup handle 20 is in this "handle retracted" position. When cup handle 20 is urged upwardly, the support members 27, 28 resiliently allow the distal end 22 of the cup handle 20 to move away for the top surface 15 of the wall recess 12 and out of the top surface indent 16. In this fashion, the ridge 25 may be rotated downwardly to the point that it engages a second indent 14 which is formed within the back surface 13 of the wall recess 12. The cup handle 20 is thereby securely retained in its generally perpendicular position relative to the cup sidewall 19. See FIG. 3. After collection of the sample, the cup handle 20 may be urged downwardly to release the ridge 25 ofthe proximal handle portion 21 from the back surface indent 14 thereby allowing the cup handle 20 to rotate downwardly to its fully retracted position.

It should also be understood that, although the preferred embodiment of the device of the present invention includes a ridge 25 formed within the proximal end 21 of the handle 20 and a pair of indents 14, 16 formed within the sidewall recess 12, another embodiment could be configured instead with an indent formed within the proximal end of the cup handle 20 and a pair of cooperating ridges formed within the sidewall recess 12.

In application, the specimen collection cup 10 may be heat sealed within a polyvinyl chloride plastic pouch (not shown) to protect against contamination. A quantity of individually packaged cups 10 could then be placed in a self-shipping carton to facilitate shipment and storage. Alternatively, the cups 10 may be sterilized at that point in the manufacturing process when the cup covers 8 are attached and then simply boxed, unwrapped, in bulk storage containers. The specimen cup 10, once removed from its sterilized pouch, is held and the threaded cover 8 is twisted and removed from the collection cup 10 and placed to the side. The cup handle 20 is urged upwardly at its distal end 22 such that the ridge 25 at the proximal end 21 of the handle 20 disengages the indent 16 contained within the top surface 15 of the sidewall recess 12. The distal end 22 of the cup handle 20 is urged upwardly until the ridge 25 at the proxinal end 21 of the handle 20 engages the indent 14 contained within the back surface 13 of the wall recess 12. During this handle 20 raising process, the handle support members 27, 28 are resiliently deformed by an approximate 90° rotation of the handle 20. The cup 10 is then ready for specimen collection. Once collected, the cup cover 8 may be replaced and the cup handle 20 urged downwardly. This downward movement of the distal end 22 of the cup handle 20 effectively disengages the ridge 25 from the indent 14 contained within the back surface 13 of the wall recess 12 and allows the handle 20 to be rotated to the point that it is securely retained in it retracted position within the wall recess 12. During this handle 20 lowering process, tie handle support members 27, 28 are resiliently deformed back to their original position prior to the handle 20 being raised.

From the foregoing detailed description of the illustrative embodiment of the invention set forth herein, it will be apparent that there has been provided a new, useful and uncomplicated urine specimen collection cup. This new specimen collection cup eliminates the inconvenienes of prior devices,reduces the likelihood of contamination, and the incidence of ineffective results common with conventional urine collection devices. It is also disposable. The new specimen collection device allows the patient to hold the cup more easily in specimen-collecting relation to their body and reduces patients' fear of dropping the collection. In this manner the specimen collection device reduces the stress associated with medical examinations. The features described in the foregoing detailed description and summarized herein reduce the possibility of needing to repeat urine samples and reduce the cost to patients insurance companies and health care providers.

The principles of this invention having been fully explained in connection with the foregoing, I hereby claim as my invention:

1. A collection device to assist with the collection of urine specimens comprising a cup member, said cup member having a continuous sidewall and being functionally adapted to collect and retain a volume of urine therewithin, a cup opening, said cup opening being functionally adapted to allow the flow of urine therethrough, a longitudinally extending cup handle, said cup handle being formed integrally with said cup sidewall and being locatable immediately adjacent said cup sidewall, means for resiliently permitting movement of the cup handle with respect to the sidewall, means for releasably securing the cup handle in a generally perpendicular cup-holding position, and means for releasably securing the cup handle in a position generally parallel to the cup sidewall.

2. The collection device of claim 1 wherein said cup handle includes a distal handle portion and proximal handle portion and said means for resiliently permitting cup handle movement includes a resilient attachment means interposed between the proximal handle portion and a portion of the cup sidewall.

3. The collection device of claim 2 wherein said cup sidewall includes a recess defined within said sidewall and said cup handle is disposed within said sidewall recess.

4. The collection device of claim 3 wherein said means for releasably securing the cup handle in a position generally parallel to the cup sidewall and in a position generally perpendicular to the cup sidewall includes a handle securing mechanism which is integrally formed within said proximal handle portion and said sidewall recess.

5. The collection device of claim 4 wherein said means for releasably securing the cup handle in a position generally parallel to the cup sidewall and in a position generally perpendicular to the cup sidewall includes a ridge defined within said proximal handle portion and a pair of cooperating indents defined within the sidewall recess whereby the handle is releasably securable in one of two positions.

6. The collection device of claim 5 wherein the cup member and handle are formed of a plastic material.

7. The collection device of claim 6 wherein the cup member and handle are formed of a plastic material.

8. The urine specimen collection device comprising
- a urine collecting cup, said cup having a first end which is open, a second end which is closed, and a generally cylindrically shaped continuous closed sidewall extending between the first open end and the second closed end of the cup, said first end being functionally adapted to allow the flow of urine therethrough,
- a longitudinally extending cup handle, said handle being formed integrally with said cup sidewall,
- means for locating said handle immediately adjacent said cup sidewall,
- means for resiliently permitting movement of the handle with respect to the cup sidewall and
- means for releasably securing the cup handle in a generally perpendicular position relative to the cup sidewall.

9. The collection device of claim 8 wherein said cup handle includes a distal handle portion and a proximal handle portion.

10. The collection device of claim 9 wherein said means for releasably securing cup handle includes a means for attaching the proximal portion of the cup handle to the cup sidewall interposed between the proximal portion of the cup handle and a portion of the cup sidewall.

11. The collection device of claim 10 wherein said means for releasably securing the cup handle includes a pair of handle support arms located between the proximal portion of the cup handle and the cup sidewall and further being integrally formed therebetween.

12. The collection device of claim 11 wherein said cup sidewall includes a recess defined within said sidewall and said cup handle is disposed within said sidewall recess.

13. The collection device of claim 12 wherein said means for releasably securing the cup handle in a generally perpendicular position includes a handle securing mechanism which is integrally formed within said proximal handle portion and said sidewall recess.

14. The collection device of claim 13 wherein said means for releasably securing the cup handle in a generally perpendicular position includes a ridge defined within said proximal handle portion and a pair of cooperating indents defined within the sidewall recess whereby the handle is releasably securable in one of two positions.

15. The collection device of claim 14 wherein the cup and handle are formed of a plastic material.

16. The collection device of claim 15 wherein the cup and handle are formed of polystyrene, polypropylene or polyethylene.

17. A urine specimen collecting device comprising
- a collection cup with a generally cylindrical sidewall, a first open end and a second closed end,
- a sidewall recess within the sidewall having a pair of side surfaces, a top surface and a back surface,
- an indent within the top surface,
- an indent within the back surface,
- a pair of plastically deformable resilient attachment members, and
- a cup handle formed integrally within the sidewall recess with a distal end and a proximal end having a ridge, the cup handle integrally formed between the attachment members,
- wherein the attachment members plastically deform such that the distal end of the cup handle pivots around said attachment members until the ridge of the proximal end snaps into the indent within the back surface of the recess, securing the cup handle in a generally perpendicular position relative to the sidewall of the cup.

* * * * *